(12) United States Patent
Frick et al.

(10) Patent No.: US 6,277,831 B1
(45) Date of Patent: Aug. 21, 2001

(54) 1,4-BENZOTHIAZEPINE-1,1-DIOXIDE DERIVATIVES SUBSTITUTED BY SUGAR RESIDUES, PROCESS FOR THEIR PREPARATION, PHARMACEUTICALS COMPRISING THESE COMPOUNDS, AND THEIR USE

(75) Inventors: Wendelin Frick, Hünstetten-Beuerbach; Heiner Glombik, Hofheim; Hubert Heuer, Schwabenheim; Hans-Ludwig Schäfer, Hochheim, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/545,456

(22) Filed: Apr. 7, 2000

(30) Foreign Application Priority Data

Apr. 9, 1999 (DE) ................................ 199 16 108

(51) Int. Cl.⁷ ...................... A61K 31/7028; A61K 31/55
(52) U.S. Cl. .................. 514/43; 514/211; 536/29.11; 540/551; 540/552
(58) Field of Search ............. 536/29.11; 514/43, 514/211; 540/551, 552

(56) References Cited

U.S. PATENT DOCUMENTS 5,859,240 * 1/1999 Brieaddy .................. 540/552
6,020,330 * 1/2000 Enhsen et al. ............ 514/211

FOREIGN PATENT DOCUMENTS 0 864 582 A2   9/1998 (EP).
96 05188 A1    2/1996 (WO).

* cited by examiner

*Primary Examiner*—Gary Geist
*Assistant Examiner*—Leigh C. Maier
(74) *Attorney, Agent, or Firm*—Finnegan, Henderson, Farabow, Garrett and Dunner, L.L.P.

(57) ABSTRACT

The invention relates to substituted 1,4-benzothiazepine-1, 1-dioxide derivatives and their acid addition salts.

1,4-Benzothiazepine-1,1-dioxide derivatives of formula 1,

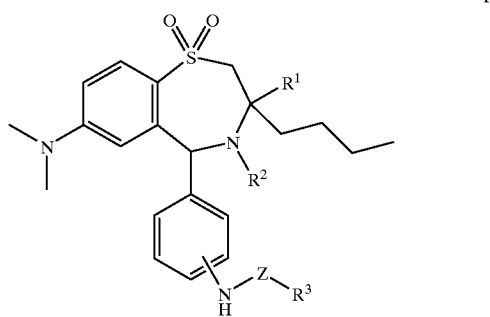

I wherein $R^1$, $R^2$, $R^3$, and Z have the meanings indicated in the specification, physiologically tolerable salts, and physiologically functional derivatives thereof, and also processes for their preparation, are described. The compounds are suitable, for example, as hypolipidemics.

12 Claims, No Drawings

1,4-BENZOTHIAZEPINE-1,1-DIOXIDE DERIVATIVES SUBSTITUTED BY SUGAR RESIDUES, PROCESS FOR THEIR PREPARATION, PHARMACEUTICALS COMPRISING THESE COMPOUNDS, AND THEIR USE

The invention relates to substituted 1,4-benzothiazepine-1,1-dioxide derivatives, their physiologically tolerable salts and physiologically functional derivatives.

1,4-Benzothiazepine-1,1-dioxide derivatives and their use for the treatment of hyperlipidemia and also arteriosclerosis and hypercholesterolemia have already been described (PCT Application No. PCT/GB 95101884, Publication No. WO 96/05188).

The invention is based on the object of making available further compounds with therapeutically valuable hypolipidemic action. In particular, the object consists in finding novel compounds which cause a higher excretion of bile acid, even at a lower dosage, compared with compounds previously known.

The invention therefore relates to compounds of formula I

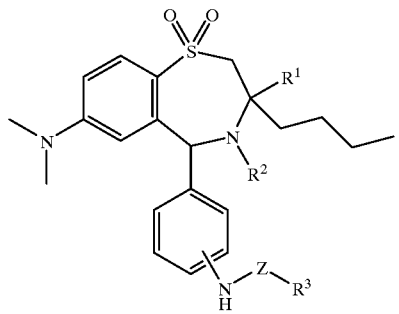

wherein:
$R^1$ is methyl, ethyl, propyl, or butyl;
$R^2$ is H or OH;
$R^3$ is a sugar residue, disugar residue, trisugar residue, or tetrasugar residue, wherein the sugar residue, disugar residue, trisugar residue, or tetrasugar residue are optionally mono- or polysubstituted by a sugar protective group;
Z is $-(C=O)_n\text{-}C_0\text{-}C_{16}\text{-alkyl-}$, $-(C=O)_n\text{-}C_0\text{-}C_{16}\text{-alkyl-NH}-$, $-(C=O)_n\text{-}C_0\text{-}C_{16}\text{-alkyl-O}-$, $-(C=O)_n\text{-}C_1\text{-}C_{16}\text{-alkyl-}(C=O)_m$, or a covalent bond;
n is 0 or 1;
m is 0 or 1;
or a pharmaceutically tolerable salt, or a physiologically functional derivative thereof.

Preferred compounds of formula I are those wherein one or more radical(s) has, or have, the following meaning(s):
$R^1$ is ethyl, propyl, or butyl;
$R^2$ is H or OH;
$R^3$ is a sugar residue or disugar residue, wherein the sugar residue or disugar residue are optionally mono- or polysubstituted by a sugar protective group;
Z is $-(C=O)_n\text{-}C_0\text{-}C_{16}\text{-alkyl-}$, $-(C=O)_n\text{-}C_0\text{-}C_{16}\text{-alkyl-NH}-$, $-(C=O)_n\text{-}C_0\text{-}C_{16}\text{-alkyl-O}-$, $-(C=O)_n\text{-}C_1\text{-}C_{16}\text{-alkyl-}(C=O)_m$, or a covalent bond;
n is 0 or 1;
m is 0 or 1;
or a pharmaceutically tolerable salt thereof.

Another embodiment of formula I are those wherein one or more radical(s) has, or have, the following meaning(s):
$R^1$ is ethyl or butyl;
$R^2$ is H or OH;
$R^3$ is a sugar residue, wherein the sugar residue is optionally mono- or polysubstituted by a sugar protective group;
Z is $-(C=O)-C_0\text{-}C_4\text{-alkyl}$ or a covalent bond;
or a pharmaceutically tolerable salt thereof.

Because of their higher water solubility compared with the starting or base compounds, pharmaceutically tolerable salts are particularly suitable for medicinal applications, where salts must have a pharmaceutically tolerable anion or cation.

Suitable pharmaceutically tolerable acid addition salts of the compounds according to the invention are salts of inorganic acids, such as hydrochloric, hydrobromic, phosphoric, metaphosphoric, nitric, sulfonic, and sulfuric acids, and also organic acids, such as acetic, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric, and trifluoroacetic acids. For medicinal purposes, the chlorine salt is preferably used. Suitable pharmaceutically tolerable basic salts are ammonium, alkali metal (such as sodium and potassium), and alkaline earth metal (such as magnesium and calcium).

Salts with a nonpharmaceutically tolerable anion are likewise within the scope of the invention as useful intermediates for the preparation or purification of pharmaceutically tolerable salts and/or for use in nontherapeutic, for example in vitro, applications.

The term "physiologically functional derivative" used here designates any physiologically tolerable derivative of a compound according to the invention, e.g., an ester which on administration to a mammal, such as man, is able (directly or indirectly) to form such a compound or an active metabolite thereof.

A further aspect of this invention is prodrugs of the compounds according to the invention. Such prodrugs can be metabolized in vivo to give a compound according to the invention. These prodrugs can themselves be active or inactive.

The compounds according to the invention can also be present in various polymorphic forms, e.g., as amorphous and crystalline polymorphic forms. All polymorphic forms of the compounds according to the invention are within the scope of the invention and are a further aspect of the invention.

Below, all references to "compound(s) according to formula I" relate to compound(s) of formula I as described above, and to their salts, solvates, and physiologically functional derivatives as described herein.

The amount of a compound according to formula I which is necessary in order to achieve the desired biological effect is dependent on a number of factors, e.g., the chosen specific compound, the intended use, the manner of administration, and the clinical condition of the patient.

In general, the daily dose lies in the range from 0.1 mg to 100 mg (typically from 0.1 mg to 50 mg) per day per kilogram of body weight, e.g., 0.1–10 mg/kg/day. Tablets or capsules can contain, for example, from 0.01 mg to 100 mg, typically from 0.02 mg to 50 mg. In the case of pharmaceutically tolerable salts, the abovementioned weight data relate to the weight of the benzothiazepine ion derived from the salt. For the prophylaxis or therapy of the abovementioned conditions, compounds according to formula I can be used directly, but they are preferably present with a tolerable carrier in the form of a pharmaceutical composition. The carrier must of course be tolerable, in the sense that it is compatible with the other constituents of the composition and is not harmful to the health of the patient. The carrier can be a solid or a liquid or both and is preferably formulated with the compound as an individual dose, for example as a tablet, which can contain from 0.05% to 95% by weight of the active compound. Further pharmaceutically active substances can likewise be present, including further compounds according to formula I. The pharmaceutical compositions according to the invention can be prepared by one of the known pharmaceutical methods, which essentially consist in mixing the constituents with pharmacologically tolerable carrier, and/or excipients.

Pharmaceutical compositions according to the invention are those which are suitable for oral and peroral (e.g., sublingual) administration, although the most suitable manner of administration in each individual case will be determined by the nature and the severity of the condition to be treated and on the type of the compound according to formula I used in each case. Sugar-coated formulations and sugar-coated sustained release formulations are also within the scope of the invention. Acid-resistant and enteric formulations are preferred. Suitable enteric coatings include cellulose acetate phthalate, polyvinyl acetate phthalate, hydroxypropylmethylcellulose phthalate, and anionic polymers of methacrylic acid and methyl methacrylate.

Suitable pharmaceutical compounds for oral administration can be present in separate units, such as capsules, cachets, lozenges, or tablets, as powders or granules, as a solution or suspension in an aqueous or nonaqueous liquid, or as an oil-in-water or water-in-oil emulsion, which in each case contain a certain amount of the compound according to formula I. These compositions can be prepared according to any suitable pharmaceutical method which comprises a step in which the active compound and the carrier (which can consist of one or more additional constituents) are brought into contact. In general, the compositions are prepared by uniform and homogeneous mixing of the active compound with a liquid and/or finely divided solid carrier, after which the product, if necessary, is shaped. Thus, a tablet can be prepared by compressing or shaping a powder or granules of the compound, if appropriate with one or more additional constituents. Pressed tablets can be prepared by tableting the compound in free-flowing form, such as a powder or granules, if appropriate mixed with a binder, lubricant, inert diluent, and/or one or more surface-active/dispersing agent (s) in a suitable machine. Shaped tablets can be prepared by shaping the pulverulent compound, moistened with an inert liquid diluent, in a suitable machine.

Pharmaceutical compositions which are suitable for peroral (sublingual) administration include lozenges, which contain a compound according to formula I with a flavoring, such as sucrose and gum arabic or tragacanth, and pastilles comprising the compound in an inert base such as gelatin and glycerol or sucrose and gum arabic.

The invention furthermore relates both to isomeric mixtures of formula I and to pure stereoisomers of formula I, and also to diastereomeric mixtures of formula I and pure diastereomers. The separation of the mixtures is carried out chromatographically.

Racemic and enantiomerically pure compounds of formula I having the following structure are preferred:

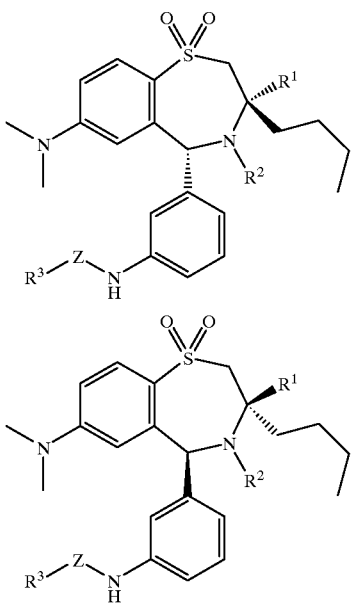

Sugar residues are understood as meaning compounds which are derived from aldoses and ketoses having 3 to 7 carbon atoms, which can belong to the D or L series; these also include amino sugars, sugar alcohols, or sugar acids. Examples are glucose, mannose, fructose, galactose, ribose, erythrose, glyceraldehyde, sedoheptulose, glucosamine, galactosamine, glucuronic acid, galacturonic acid, gluconic acid, galactonic acid, mannonic acid, glucamine, 3-amino-1,2-propanediol, glucaric acid, and galactaric acid.

Disugars are intended to mean saccharides which have two sugar units. Di-, tri-, or tetrasaccharides are formed by acetal-like bonding of 2 or more sugars. The bonds can occur in the a or 0 form. Some examples are lactose, maltose, and cellobiose.

If the sugar is substituted, the substitution preferably takes place on the hydrogen atom of an OH group of the sugar.

The following protective groups are suitable for the hydroxyl groups of the sugars: benzyl, acetyl, benzoyl, pivaloyl, trityl, tert-butyidimethylsilyl, benzylidene, cyclohexylidene, or isopropylidene protective groups.

Compounds of formula I and their pharmaceutically tolerable salts and physiologically functional derivatives are ideal pharmaceuticals for the treatment of lipid metabolism disorders, in particular of hyperlipidemia. The compounds of formula I are likewise suitable for influencing the serum cholesterol level and for preventing and treating arteriosclerotic symptoms. The compounds can optionally also be administered in combination with statins, such as simvastatin, fluvastatin, pravastatin, cerivastatin, lovastatin, or atorvastatin. The following data confirm the pharmacological activity of compounds according to the invention.

The biological testing of compounds according to the invention was carried out by means of a perfusion test. This test investigates the action of the compounds on the bile acid transport in the ileum. The diastereomeric mixtures of the compounds were tested unless indicated otherwise.

The Perfusion Test was Carried Out as Described Below:

Experimental Methods

Male Wistar rats (weight range 250–350 g) were anesthetized with urethane (1.5 g/kg i.p.) and the bile duct was cannulated with a polyethylene tube. Eight centimeters proximal to the ileocecal flap, an incision was made into the ileum and a silicone adapter for tubes was sewn in. A second incision with implantation of a corresponding silicone adapter was made in the cecum. Silicone tubes were attached to the adapter in order to perfuse the ileum in an orthograde and open manner (nonrecirculating) with perfusion buffer at a perfusion rate of 1 ml/min.

The perfusion tubes were filled with perfusion buffer (137 mM NaCl, 0.9 mM $CaCl_2$, 0.51 mM $MgCl_2$, 8.1 mM $Na_2HPO_4$, 2.7 mM KCl, 1.47 mM $KH_2PO_4$) (pH 7.4), 1% (v/v) ethanol, and 1% DMSO. The perfusion buffer contained the test compounds in concentrations as indicated, or the vehicle alone. The buffer was preheated to 37° C. The perfusion buffer contained 3 mM taurocholic acid (TCA), which in turn was labeled with 1000 dpm/μl of $^3H$ TCA as a marker.

Study Design and Evaluation of the Results

An experimental batch was chosen which allowed the determination of the inhibition of bile acid transport in the individual animal. The bile was collected at 10 min intervals over a period of 90 min (in the case of a following wash-out phase for testing the reversibility over a period of up to 160 min). The perfusion of the vehicle-containing buffer solution over a period of 40 min (pre-test substance) was followed by a perfusion with perfusion buffer which contained the test compound in the concentration to be tested (to 90 min).

For the calculation of the percentage inhibition by the test compound, the dpms (disintegrations per min of $^3H$-TCA) in the bile from 80–90 min (end of the perfusion with the test substance) were related to the collection period 30–40 min during the preliminary phase, when the excretion of the $^3H$-TCA in the control phase had reached its maximum and plateau. The $EC_{50}$ (=effective concentration 50) was calculated as the effective concentration between the inhibitory values of different concentrations which inhibited the maximum bile acid excretion by 50%.

TABLE 1

| Compounds from Example | $EC_{50}$ Ileum perfusion (μM) |
| --- | --- |
| 1 | 0.09 |
| 2 | 0.15 |
| 3 | 0.22 |
| 4 | 0.72 |
| 5 | 0.4 |
| 6 | 0.09 |
| 7 | 1.4 |
| Comparison Example 8 | 9.8 |

Results

From the data shown above in Table 1, compounds of formula I according to the invention have an action which is better by a factor of 7 to 100 relative to the compounds previously known.

The following examples serve to illustrate the invention in greater detail, without restricting the invention to products and embodiments specifically described in the examples.

EXAMPLE 1 a

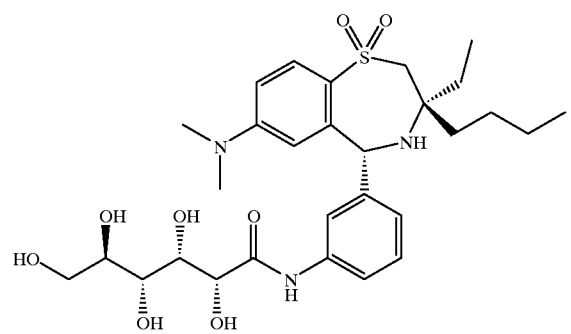

b

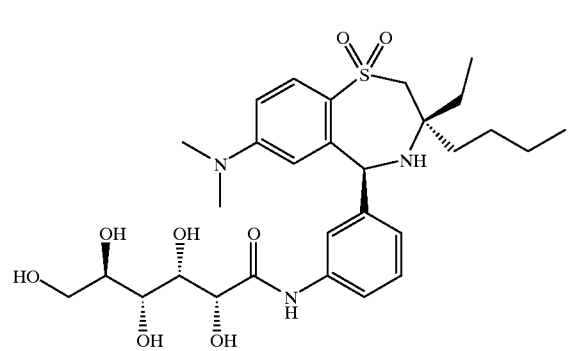

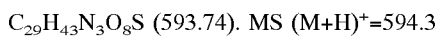

$C_{29}H_{43}N_3O_8S$ (593.74). MS $(M+H)^+$=594.3

EXAMPLE 2 a

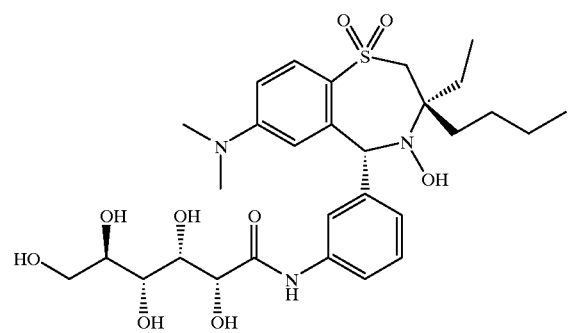

b

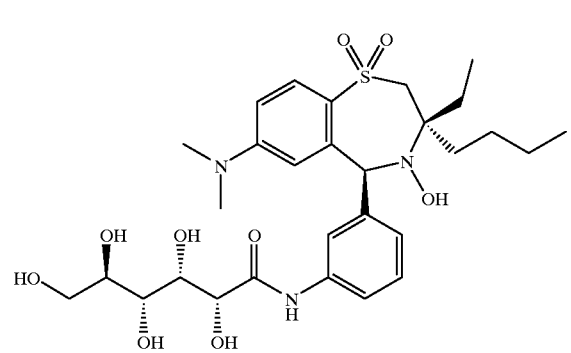

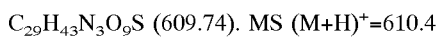

$C_{29}H_{43}N_3O_9S$ (609.74). MS $(M+H)^+$=610.4

EXAMPLE 3
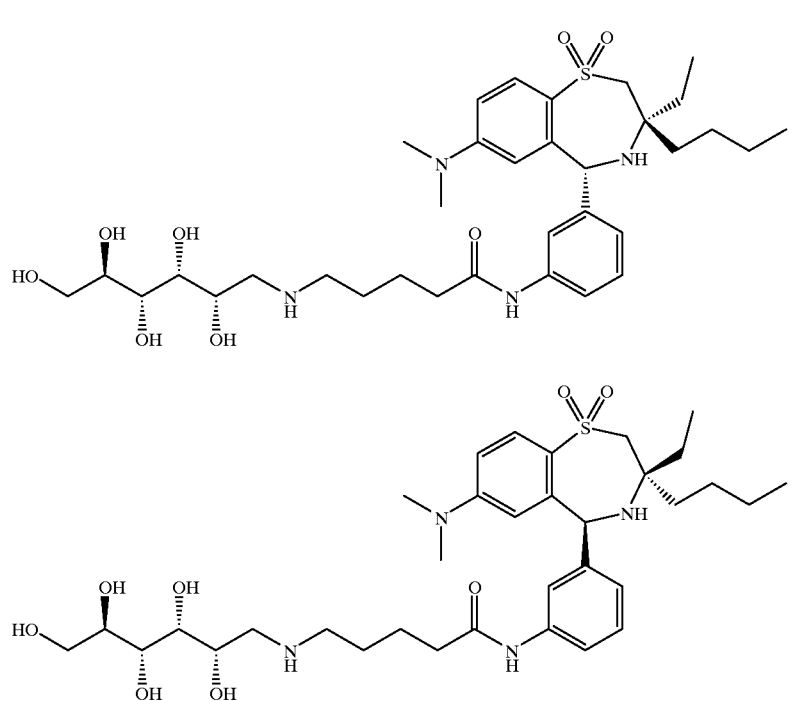
C$_{34}$H$_{54}$N$_4$O$_8$S (678.89). MS (M+H)$^+$=679.4
EXAMPLE 4
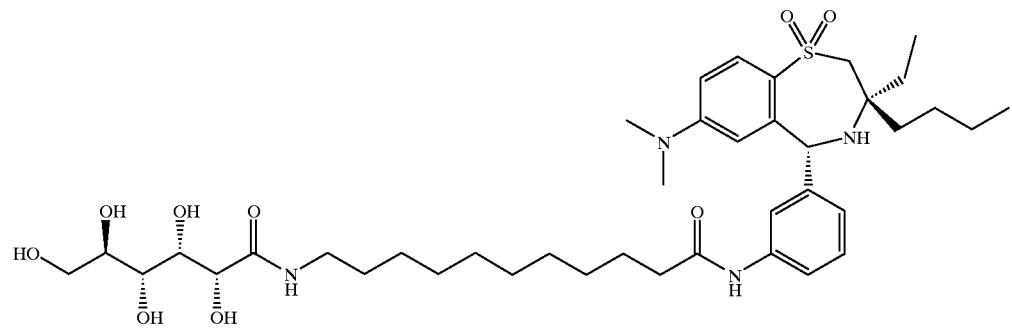
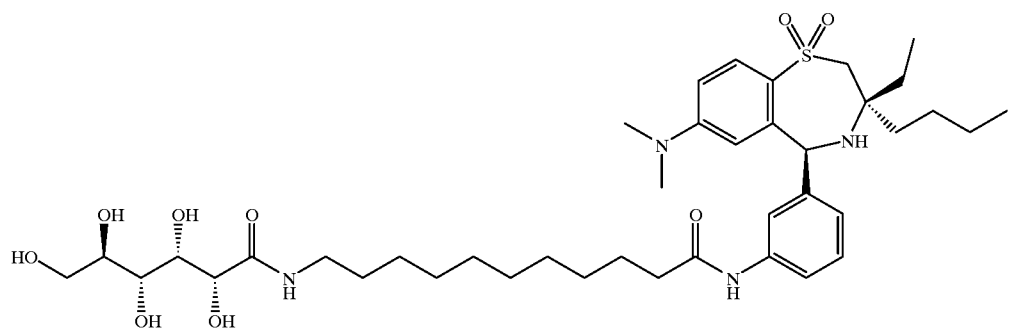
C$_{40}$H$_{64}$N$_4$O$_9$S (777.03). MS (M+H)$^+$=777.6

EXAMPLE 5
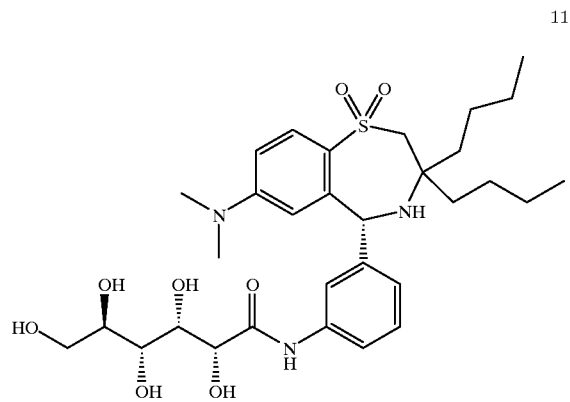
11a
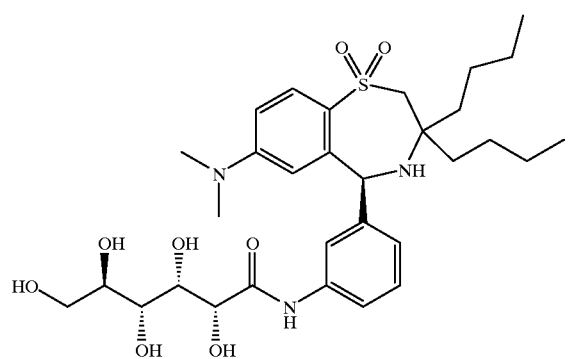
11b
$C_{31}H_{47}N_3O_8S$ (621.79). MS $(M+H)^+=622.4$
EXAMPLE 6
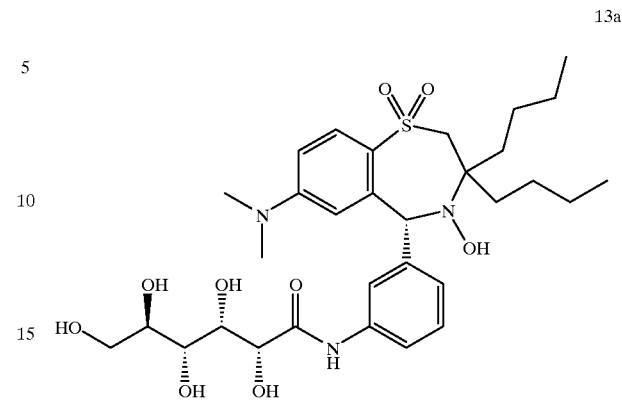
13a
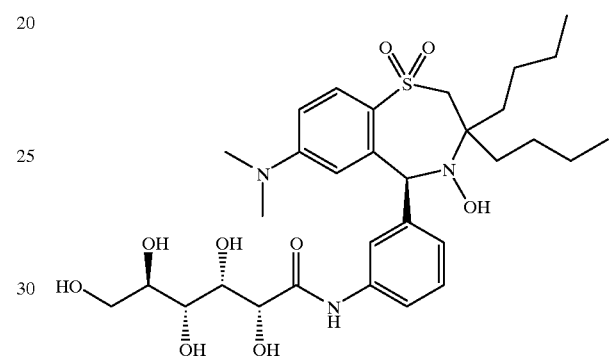
13b
$C_{31}H_{47}N_3O_9S$ (637.79). MS $(M+H)^+=638.5$
EXAMPLE 7
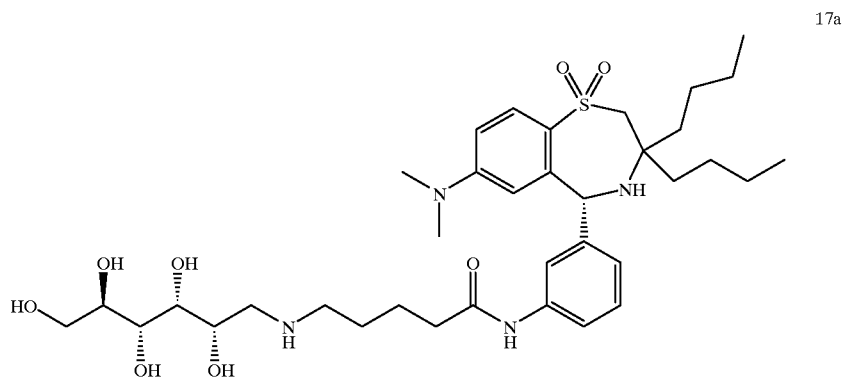
17a

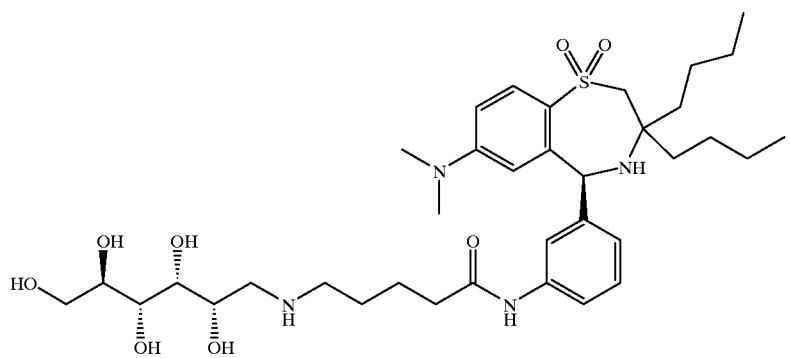
$C_{36}H_{58}N_4O_8S$ (706.94). MS $(M+H)^+$=707.6
Comparison example from WO 96/05188 (Example No. 20, 264W94, Glaxo Wellcome):
Comparison Example 8
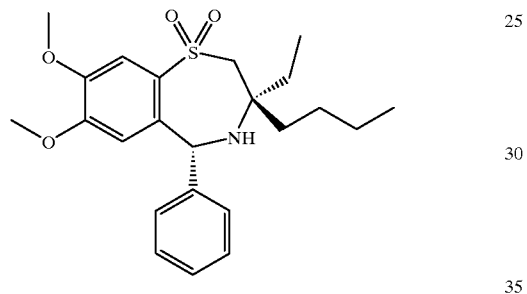
The examples were prepared according to Schemes 1 and 2 as shown below.
Scheme 1
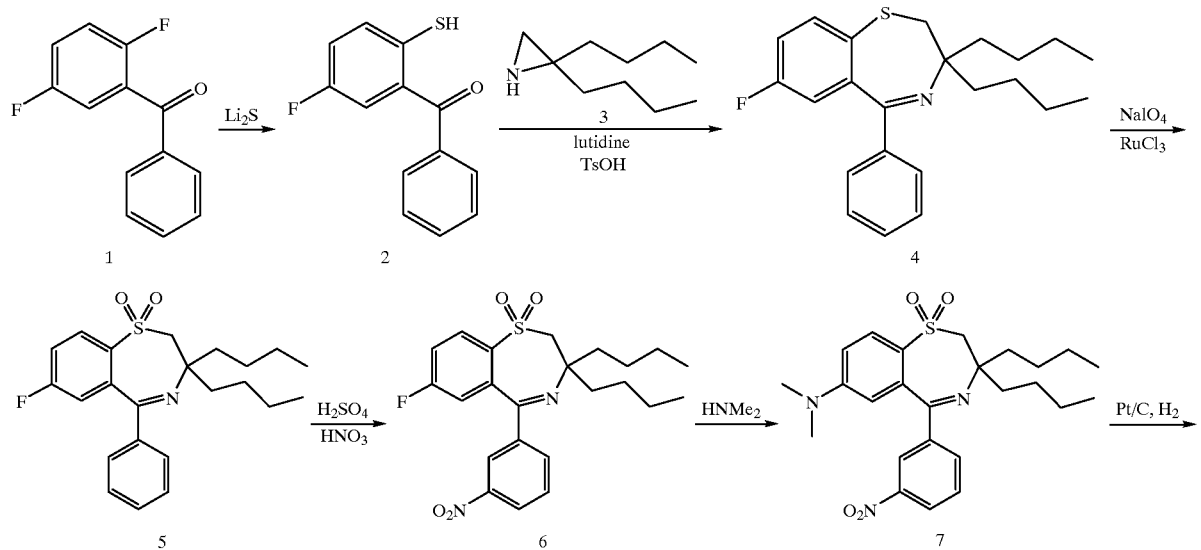

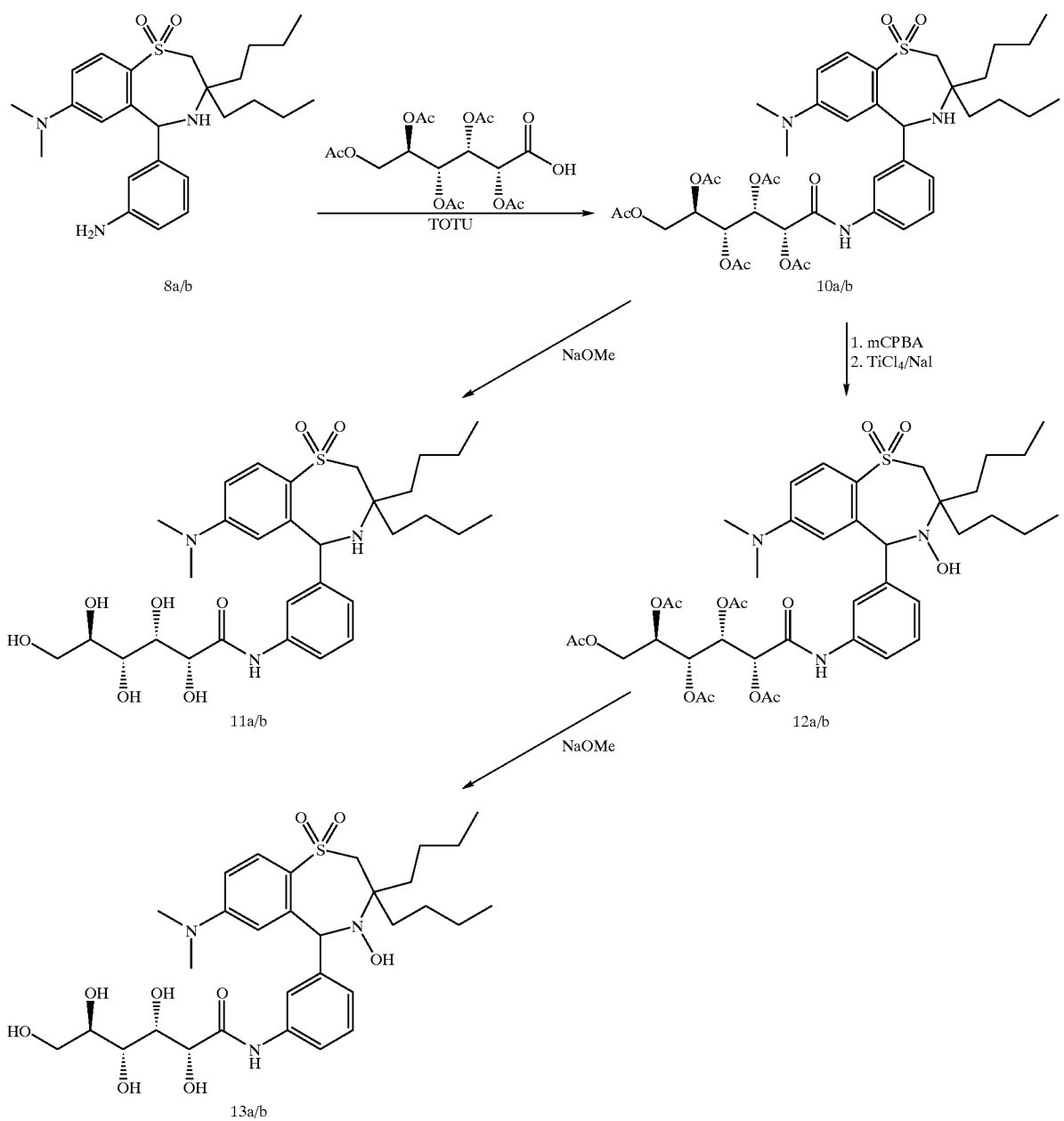
Scheme 2
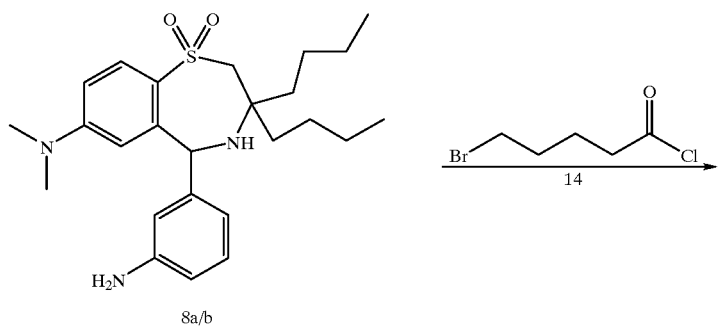

-continued
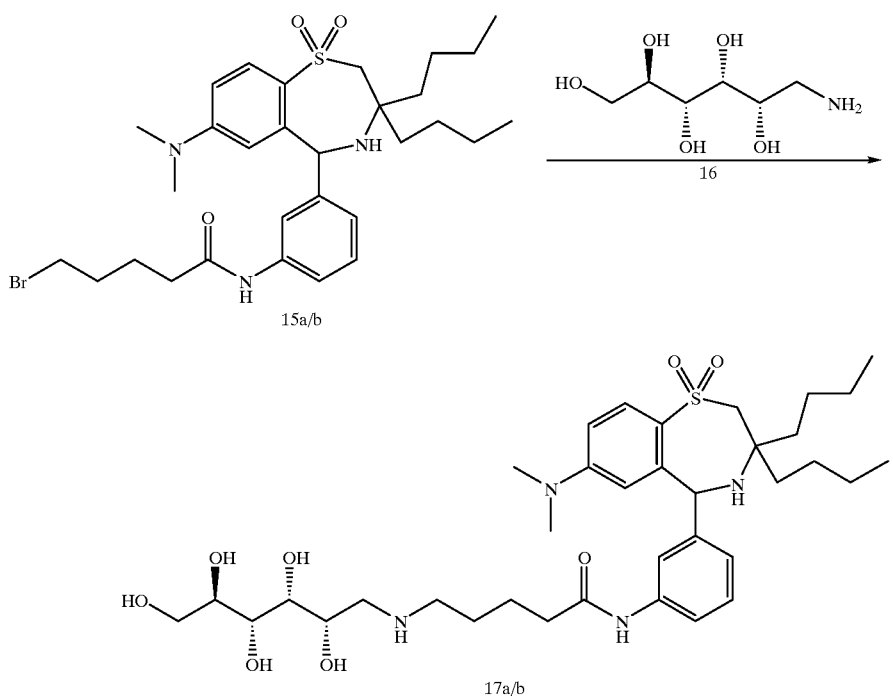
Scheme 3
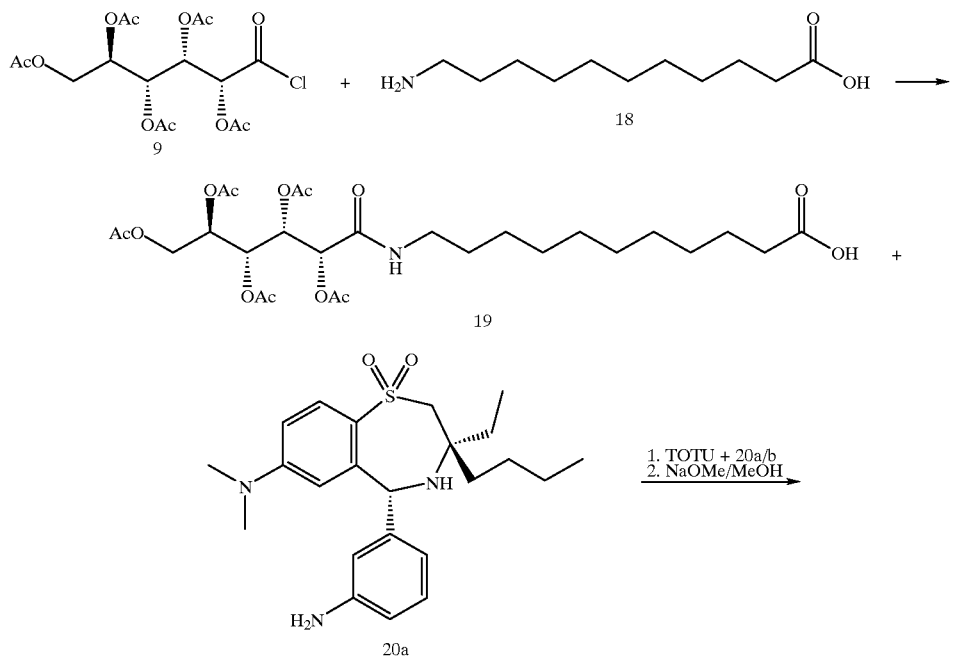

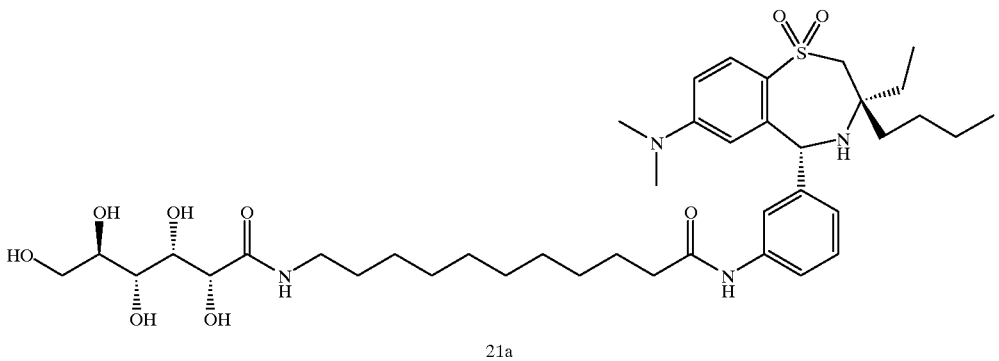

21a

Synthesis of Compound 2:

20 g (91.6 mmol) of 2,5-difluorobenzophenone 1 (Fluka) was dissolved in 400 ml of DMSO. 7.0 g (150 mmol) of lithium sulfide (Fluka) was added under argon. After three hours at 120° C., the mixture was allowed to cool to room temperature. It was shaken with 200 ml of 2 M HCl aq. and 500 ml of ethyl acetate. The organic phase was washed twice with NaCl solution, dried over $MgSO_4$, filtered, and concentrated. 24 g of crude product 2 was obtained as a reddish oil. TLC (n-heptanelethyl acetate 3:1) gave $R_f$=0.3 (starting material 1 $R_f$=0.4). $C_{13}H_9FOS$ (232.28). MS $(M+H)^+$=233.1.

Synthesis of Compound 4:

7 g of crude product 2, 2.5 g (16 mmol) of dibutylaziridine 3 (R. Gauthier et al., *J. Organomet. Chem.* 140 (1977) 245–255) and 300 mg of p-toluenesulfonic acid were dissolved in 100 ml of lutidine. The reaction solution was boiled in a water separator for three hours. It was then concentrated and the residue was purified by flash chromatography. Yield 3.6 g (61%) of 4 as a colorless oil. TLC (n-heptane/ethyl acetate 9:1) gave $R_f$=0.5. $C_{23}H_{28}FNS$ (369.55). MS $(M+H)^+$=370.3.

Synthesis of Compound 5:

3.6 g (9.7 mmol) of 4 and 6.0 g of $NaIO_4$ were suspended in 100 ml of acetonitrile, 50 ml of methylene chloride, and 30 ml of water. After addition of 200 mg of $RuCl_3$, the mixture was stirred vigorously at room temperature for 2 hours. The solution was diluted with 200 ml of ethyl acetate and washed twice with NaCl solution. After drying over $MgSO_4$, it was concentrated and purified by flash chromatography. Yield 3.47 g (89%) of 5 as an amorphous solid. TLC (n-heptane/ethyl acetate 4:1) gave $R_f$=0.5 (starting material 4 $R_f$=0.6). $C_{23}H_{28}FNO_2S$ (401.55). MS $(M+H)^+$=402.2.

Synthesis of Compound 6:

3.47 g (8.6 mmol) of 5 was dissolved in 24 ml of nitrating acid (from 14 ml of $HNO_3$ and 10 ml of $H_2SO_4$). The reaction temperature was kept at 20° C. by cooling. After 30 minutes, the solution was poured onto a mixture of 700 g of ice and 200 ml of ethyl acetate. The aqueous phase was separated off and washed carefully four times with 150 ml of saturated $NaHCO_3$ solution, then dried over $MgSO_4$, concentrated, and purified by flash chromatography. Yield 3.0 g (78%) of 6 as an amorphous solid. TLC (n-heptanelethyl acetate 4:1) gave $R_f$=0.4. $C_{23}H_{27}N_2O_4SF$ (446.54). MS $(M+H)^+$=447.2.

Synthesis of Compound 7:

3.0 g (6.7 mmol) of 6 was dissolved in 50 ml of 33% strength $HNMe_2$ in ethanol (Fluka) and the solution was stirred at 50° C. for one hour. It was then allowed to cool to room temperature and the resulting product was filtered. Yield 2.86 g (90%) of 7, yellowish crystals m.p. 188° C. TLC (n-heptane/ethyl acetate 2:1) gave $R_f$=0.5 (starting material 7 $R_f$=0.6). $C_{25}H_{33}N_3O_4S$ (471.62). MS $(M+H)^+$=472.3.

Synthesis of Compound 8a/b as an Enantiomeric Mixture:

1.05 g (2.2 mmol) of 7 was suspended in 30 ml of toluene and 500 mg of platinum on active carbon (10% strength) was added. The mixture was hydrogenated in a shaking autoclave for 30 hours at 150 bar hydrogen pressure and 100° C. For work-up, the mixture was filtered through silica gel, which was washed with 100 ml of methanol, the filtrate was concentrated, and the residue was purified by flash chromatography. Yield 495 mg (48%) of 8a/b as an amorphous solid. TLC (n-heptane/ethyl acetate 1:1) gave $R_f$=0.3. $C_{25}H_{37}N_3O_2S$ (443.65). MS $(M+H)^+$=444.3.

Synthesis of Compound 10a/b as a Diastereomeric Mixture:

80 mg (0.18 mmol) of 8a/b and 100 mg (0.24 mmol) of penta-O-acetyl-D-gluconic acid (*Org. Synth.* Vol. 5, 887) were dissolved in 4 ml of DMF (dimethyl formamide). 100 mg (0.3 mmol) of TOTU (Fluka), 35 mg (0.24 mmol) of oxime (ethyl hydroxyiminocyanoacetate; Fluka), and 0.1 ml (0.78 mmol) of HEM (4-ethylmorpholine) were added successively. After one hour at room temperature, the mixture was diluted with 20 ml of ethyl acetate and washed three times with water. The organic phase was dried over $MgSO_4$, filtered, and concentrated. The residue was purified by means of flash chromatography (ethyl acetate/n-heptane 2:1) and 130 mg (86%) of 10a/b was obtained as an amorphous solid. TLC (ethyl acetateln-heptane 2:1) gave $R_f$=0.3. The product 10a/b has the same retention as the starting material 8a/b, but colors differently with 2 M sulfuric acid. $C_{41}H_{57}N_3O_{13}S$ (131.97). MS $(M+H)^+$=832.6.

Synthesis of Compound 11a/b as a Diastereomeric Mixture:

130 mg (0.16 mmol) of 10a/b was dissolved in 5 ml of methanol. After addition of 0.2 ml of a methanolic 1 M sodium methoxide solution, the mixture was allowed to stand at room temperature for one hour. It was then neutralized using methanolic HCl solution and concentrated. The residue was purified by flash chromatography (methylene chloride/methanollconc. ammonia 30/10/3) and 78 mg (80%) of 10a/b was obtained as an amorphous solid. TLC (methylene chloride/methanollconc. ammonia 30/10/3) gave $R_f$=0.4. $C_{31}H_{47}N_3O_8S$ (621.80). MS $(M+H)^+$=622.4.

Synthesis of Compound 12a/b as a Diastereomeric Mixture:

618 mg (0.74 mmol) of 10a/b was dissolved in 30 ml of methylene chloride and 385 ml) (2.23 mmol) of 70% strength m-chloroperbenzoic acid (Fluka) was added. After 30 minutes at room temperature, the mixture was diluted with 100 ml of ethyl acetate and washed three times with NaHCO$_3$ solution. After drying using MgSO$_4$, the mixture was concentrated and 700 mg of crude product was obtained. This crude product was dissolved in 28 ml of a 0.05 M TiCl$_4$/acetonitrile solution. After addition of 300 mg of solid NaI, the mixture was stirred for 15 minutes. For work-up, it was diluted with 150 ml of ethyl acetate and washed with 100 ml of 2 M of sodium thiosulfate solution. The organic phase was dried over MgSO$_4$ and concentrated, and the residue was purified by flash chromatography. Yield 550 mg (87% over 2 stages) of 12a/b as an amorphous solid. TLC (n-heptane/ethyl acetate 1:2) gave R$_f$=0.3 (starting material 10a/b R$_f$=0.35). C$_{41}$H$_{57}$N$_3$O$_{14}$S (847.99). MS (M+H)$^+$=848.5.

Synthesis of Compound 13a/b as a Diastereomeric Mixture:

550 mg (0.65 mmol) of 12a/b was dissolved in 20 ml of methanol. After addition of 0.3 ml of a methanolic 1 M sodium methoxide solution, the mixture was allowed to stand at room temperature for one hour. It was then neutralized using methanolic HCl solution and concentrated. The residue is purified by flash chromatography (methylene chloride/methanolconc. ammonia 30/1013) and 370 mg (89%) of 13a/b was obtained as an amorphous solid. TLC (methylene chloride/methanol/conc. ammonia 30/10/3) gave R$_f$=0.4. C$_{31}$H$_{47}$N$_3$O$_9$S (637.80). MS (M+H)$^+$=638.4.

Synthesis of Compound 15a/b as a Diastereomeric Mixture:

719 mg (1.6 mmol) of 8a/b was dissolved in 30 ml of methylene chloride and 2 ml of triethylamine. 0.5 ml (3.7 mmol) of 14 was added dropwise to this solution and it was allowed to stand at room temperature for 15 minutes. The solution was then filtered through silica gel and washed with 100 ml of ethyl acetate. After concentration, the residue was purified by flash chromatography. Yield 950 mg (95%) of 15a/b as an amorphous solid. TLC (n-heptane/ethyl acetate 1:1) gave R$_f$=0.4. C$_{30}$H$_{44}$BrN$_3$O$_3$S (606.67). MS (M+H)$^+$=607.3.

Synthesis of Compound 17a/b as a Diastereomeric Mixture:

897 mg (1.47 mmol) of 15a/b was dissolved in 20 ml of DMF. After addition of 1.3 g (7.1 mmol) of 16 (glucamine, Fluka), the mixture was heated at 80° C. for two hours. It was then diluted with 50 ml of ethyl acetate and washed three times with water. The organic phase was dried over MgSO$_4$, filtered, and concentrated. The residue was purified by means of flash chromatography (methylene chloride/methanollconc. ammonia 30/10/3) and 700 mg (67%) of 17a/b was obtained as an amorphous solid. TLC (methylene chloride/methanol/conc. ammonia 30/10/3) gave R$_f$=0.4. C$_{36}$H$_{58}$N$_4$O$_8$S (706.95). MS (M+H)$^+$=707.4.

Synthesis of Compound 19:

8.0 g (18.8 mmol) of 9 (penta-O-acetyl-D-gluconoyl chloride; *Org. Synth.* Vol. 5, 887) was added to a suspension of 8.0 g (40 mmol) of 18 (Fluka) in 150 ml of anhydrous DMF. This suspension was vigorously stirred at room temperature for 20 hours. 500 ml of ethyl acetate and 200 ml of water were then added. The aqueous phase was extracted again with 250 ml of ethyl acetate. The combined organic phase was washed three times with sodium chloride solution, dried over MgSO$_4$, filtered, and concentrated. Yield 9.5 g (86%) of 19 as a colorless oil. TLC (methylene chloride/methanol/conc. ammonia 30/10/3) gave R$_f$=0.8. C$_{27}$H$_{43}$NO$_{13}$ (589.64). MS (M+H)$^+$=590.4.

Synthesis of Compound 21a/b as a diastereomeric mixture:

200 mg (0.34 mmol) of 19, 70 mg (0.17 mmol) of 20a/b (20a/b was prepared analogously to 8a/b by carrying out the reaction sequence of reaction scheme 1 with 2-butyl-2-ethylaziridine (R. Gauthier et al., *J. Organomet. Chem.* 140 (1977) 245–255) and 1), 240 mg of TOTU, 80 mg of oxime, and 0.3 ml of HEM were reacted in 4 ml of DMF analogously to the procedure for compound 11a/b. After flash chromatography (methylene chloride/methanol/conc. ammonia 30/5/1), 60 mg (46%, over two stages) of 21a/b was obtained as an amorphous solid. TLC (methylene chloride/methanol/conc. ammonia 30/5/1) gave R$_f$=0.2. C$_{40}$H$_{64}$N$_4$O$_9$S (777.04). MS (M+H)$^+$=777.8.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A compound of formula I

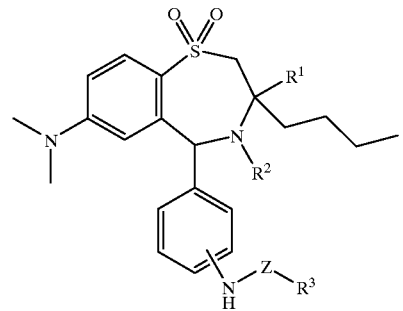

wherein:

R$^1$ is methyl, ethyl, propyl, or butyl;

R$^2$ is H or OH;

R$^3$ is a sugar residue, disugar residue, trisugar residue, or tetrasugar residue, wherein the sugar residue, disugar residue, trisugar residue, or tetrasugar residue are optionally mono- or polysubstituted by a sugar protective group;

Z is —(C═O)$_n$—C$_0$-C$_{16}$-alkyl-, —(C═O)$_n$—C$_0$-C$_{16}$-alkyl-NH—, —(C═O)$_n$—C$_0$-C$_{16}$-alkyl-O—, —(C═O)$_n$—C$_1$-C$_{16}$-alkyl-(C═O)$_m$, or a covalent bond;

n is 0 or 1;

m is 0 or 1;

or a pharmaceutically acceptable salt, or a physiologically functional derivative thereof.

2. A compound of claim 1, wherein

R$^1$ is ethyl, propyl, or butyl;

R$^2$ is H or OH;

R$^3$ is a sugar residue or disugar residue, wherein the sugar residue or disugar residue is optionally mono- or polysubstituted by a sugar protective group;

Z is —(C═O)$_n$—C$_0$-C$_{16}$-alkyl-, —(C═O)$_n$—C$_0$-C$_{16}$-alkyl-NH—, —(C═O)$_n$—C$_0$-C$_{16}$-alkyl-O—, —(C═O)$_n$—C$_1$-C$_{16}$-alkyl-(C═O)$_m$, or a covalent bond;

n is 0 or 1;

m is 0 or 1;

or a pharmaceutically acceptable salt thereof.

3. A compound of claim 1, wherein

R$^1$ is ethyl or butyl;

R$^2$ is H or OH;

R$^3$ is a sugar residue, wherein the sugar residue is optionally mono- or polysubstituted by a sugar protective group;

Z is —(C=O)—$C_0$–$C_4$-alkyl or a covalent bond;
or a pharmaceutically acceptable salt thereof.

4. A process for the preparation of at least one compound of claim 1, comprising reacting, according to the following reaction scheme

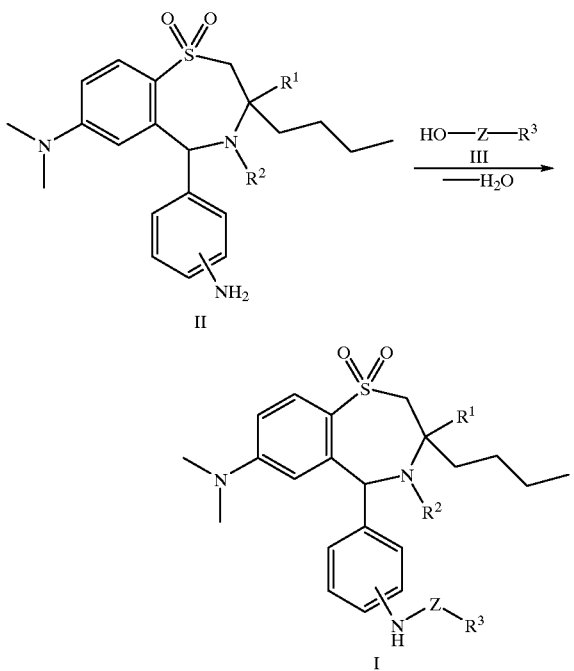

an amine of formula II, wherein $R^1$, $R^2$ and $R^3$ are defined as in claim 1, with a compound of formula III, wherein $R^3$ and Z are defined as in claim 1, removing water to give a compound of formula I, and optionally converting the compound of formula I obtained into a physiologically acceptable salt or a physiologically functional derivative thereof.

5. A pharmaceutical composition, comprising at least one compound of claim 1 and a pharmacologically acceptable carrier or excipient.

6. A pharmaceutical composition of claim 5, further comprising at least one statin.

7. The pharmaceutical composition of claim 6, wherein the statin is selected from at least one of simvastatin, fluvastatin, pravastatin, cerivastatin, lovastatin, or atorvastatin.

8. A pharmaceutical composition for the treatment of lipid metabolism disorders, comprising an effective amount of a compound of claim 1, together with a pharmacologically acceptable carrier or excipient.

9. A method for treating a lipid metabolism disorder, comprising administering to a patient in need thereof an effective amount of at least one compound of claim 1.

10. A method for treating hyperlipidemia, comprising administering to a patient in need thereof an effective amount of at least one compound of claim 1.

11. A method for maintaining or lowering serum cholesterol level, comprising administering to a patient in need thereof an effective amount of at least one compound of claim 1.

12. A method for preventing or treating arteriosclerotic symptoms, comprising administering to a patient in need thereof an effective amount of at least one compound of claim 1.

* * * * *